United States Patent
Hular et al.

(10) Patent No.: US 7,945,312 B2
(45) Date of Patent: May 17, 2011

(54) MULTISENSOR PROBE FOR TISSUE IDENTIFICATION

(75) Inventors: Richard Hular, San Carlos, CA (US); Luiz Da Silva, Danville, CA (US); Charles Chase, Dublin, CA (US)

(73) Assignee: Bioluminate, Inc., San Carlos, CA (US)

( * ) Notice: Subject to any disclaimer, the term of this patent is extended or adjusted under 35 U.S.C. 154(b) by 123 days.

(21) Appl. No.: 12/196,769

(22) Filed: Aug. 22, 2008

(65) Prior Publication Data
US 2008/0306391 A1     Dec. 11, 2008

Related U.S. Application Data (63) Continuation of application No. 11/139,904, filed on May 26, 2005, now abandoned, which is a continuation of application No. 09/947,171, filed on Sep. 4, 2001, now abandoned.

(51) Int. Cl.
*A61B 6/00* (2006.01)
*A61B 5/00* (2006.01)
(52) U.S. Cl. ............ 600/476; 600/473; 600/310
(58) Field of Classification Search .......... 600/310, 600/424, 473, 476; 356/479, 497
See application file for complete search history.

(56) References Cited

U.S. PATENT DOCUMENTS

| | | | |
|---|---|---|---|
| 5,437,283 A * | 8/1995 | Ranalletta et al. | 600/463 |
| 5,800,350 A * | 9/1998 | Coppleson et al. | 600/372 |
| 6,014,204 A * | 1/2000 | Prahl et al. | 356/73 |
| 6,047,218 A * | 4/2000 | Whayne et al. | 607/122 |
| 6,384,915 B1 * | 5/2002 | Everett et al. | 356/336 |

* cited by examiner

*Primary Examiner* — Long V Le
*Assistant Examiner* — Michael T Rozanski
(74) *Attorney, Agent, or Firm* — Morrison & Foerster LLP

(57) ABSTRACT

A multisensor probe for continuous real-time tissue identification. The multisensor probe includes a tissue penetrating needle, a plurality of sensors useful in characterizing tissue and a position sensor to measure the depth of the needle into the tissue being diagnosed. The sensors include but are not limited to an optical scattering and absorption spectroscopy sensor, an optical coherence domain reflectometry sensor, an electrical impedance sensor, a temperature sensor, a $pO_2$ sensor, a chemical sensor and other sensors useful in identifying tissue. The sensors may take the form of a plurality of optical fibers extending through said needle. A retractable sheath may be disposed around the distal section of the needle to protect the needle when not in use. The sheath retracts when the probe is inserted into tissue and the position of the sheath relative to the needle may be measured to determine the needle's depth. Systems and methods for tissue identification are also provided.

15 Claims, 8 Drawing Sheets

MULTISENSOR PROBE FOR TISSUE IDENTIFICATION

CROSS REFERENCE TO RELATED APPLICATIONS

This application is a continuation of U.S. Ser. No. 11/139,904, filed May 26, 2005, which is a continuation of U.S. Ser. No. 09/947,171, filed Sep. 4, 2001. The entire disclosures of both above-referenced applications are hereby incorporated by reference herein.

TECHNICAL FIELD

This invention is directed to tissue identification and in particular, to a multisensor probe for identifying cancerous tissue in vivo.

BACKGROUND

Every week in the United States about 19,000 open surgical breast biopsies are performed on women. Only about 3000 cancers will be found. Thus, about 85% of the biopsies are unnecessary. This means about 16,000 women will needlessly undergo open surgical breast biopsies in the U.S. every week because of the inaccuracy in diagnosing cancerous tissue in the breast.

Open surgical breast biopsies are highly undesirable because they are invasive and traumatic to the patient. In a surgical biopsy, the suspected location of the abnormality would be marked with a thin, hooked guide wire. The surgeon tracts the guide wire to the location of the suspected abnormality and the suspect area is excised. The open surgical biopsy is the most common form of biopsy and is invasive, painful and undesirable to the patient. The open surgical biopsies may also leave scar tissue which may obscure the diagnostic ability of future mammograms, creating a major handicap for the patient.

Another form of biopsy is a large-core needle biopsy (14 gauge needle). The standard core biopsies remove a 1 mm×17 mm core of tissue. The large core needle biopsy is less invasive than a surgical biopsy but still removes an undesirable amount of tissue.

Still another form of biopsy is the stereo tactic fine needle aspiration biopsy. In this type of biopsy, a small amount of the cells are aspirated for cytological analysis. This procedure is minimally invasive. A shortcoming, however, with stereo tactic biopsies is poor accuracy. The poor accuracy is a result of the small sample size which makes accurate cytology difficult.

Another drawback of typical biopsy procedures is the length of time required for the laboratory to review and analyze the excised tissue sample. The wait can take, on average, approximately two months from the first exam to final diagnosis. Consequently, many women may experience intense anxiety while waiting for a final determination.

Various methods and devices have been developed to measure physical characteristics of tissue in an effort to distinguish between cancerous and non-cancerous tissue. For example, U.S. Pat. No. 5,303,026 to Strobl et al. (the Strobl patent) describes an apparatus and method for spectroscopic analysis of scattering media such as biological tissue. More specifically, the Strobl patent describes an apparatus and method for real-time generation and collection of fluorescence, reflection, scattering, and absorption information from a tissue sample to which multiple excitation wavelengths are applied.

U.S. Pat. No. 5,349,954 to Tiemann et al. also describes an instrument for characterizing tissue. The instrument includes, amongst other things a hollow needle for delivering light from a monochromator through the needle to a desired tissue region. Mounted in the shaft of the needle is a photodiode having a light sensitive surface facing outward from the shaft for detecting back-scattered light from the tissue region.

U.S. Pat. No. 5,800,350 to Coppleson et al. discloses an apparatus for tissue type recognition. In particular, an apparatus includes a probe configured to contact the tissue and subject the tissue to a plurality of different stimuli such as electrical, light, heat, sound, magnetic and to detect plural physical responses to the stimuli. The apparatus also includes a processor that processes the responses in combination in order to categorize the tissue. The processing occurs in real-time with an indication of the tissue type (e.g. normal, pre-cancerous/cancerous, or unknown) being provided to an operator of the apparatus.

U.S. Pat. No. 6,109,270 to Mah et al. (the Mah patent) discloses a multimodality instrument for tissue characterization. In one configuration shown in the Mah patent, a system with a multimodality instrument for tissue identification includes a computer-controlled motor driven heuristic probe with a multisensory tip.

Notwithstanding the above, there still exists a need for a convenient and reliable multisensor probe that can provide real time analysis of multiple tissue properties. In particular, a multisensor probe and system in accordance with the present invention is desirable.

SUMMARY OF THE INVENTION

The present invention includes a multisensor probe for tissue identification comprising an elongate body having a distal section, a distal tip, and a lumen extending through the elongate body to the distal tip. The probe further includes an optical scattering and absorption spectroscopy (OSAS) sensor configured to deliver and receive light from the distal tip of the elongate body and a position sensor configured to measure the depth the distal tip is inserted into the tissue. Suitable position sensors include but are not limited to an optical sensor, capacitive sensor, or a resistive sensor.

A variation of the present invention includes the multisensor probe as described above wherein the probe further includes a slideable sheath coaxially disposed over the distal section of the elongate body. The sheath is retractable from the distal section as the distal section of the elongate body is inserted into the tissue. In a variation, the position sensor is configured to read the position of the sheath relative to the elongate body.

Another variation of the present invention includes the multisensor probe as described above wherein the probe further includes an electrical sensor. The electrical sensor is configured to measure electrical properties of the tissue. The electrical sensor includes a first electrically conducting element and a second electrically conducting element. The first and second electrically conducting elements extend to the distal tip of the elongate body. In a variation, the elongate body is the first conducting element. Suitable materials for the first conducting element are stainless steel, aluminum, titanium, gold, silver, and other electrically conducting materials.

Another variation of the present invention includes a multisensor probe as described above wherein the probe further includes a memory device capable of storing useful information about the probe.

Another variation of the present invention includes the multisensor probe described above wherein the probe further includes a switch or push button for marking a location in the tissue as the distal section is inserted into the tissue.

Another variation of the present invention includes the probe as described above wherein the probe further includes additional sensors. In this variation, the multisensor probe additionally includes an optical coherence domain reflectometry (OCDR) sensor having an optical fiber extending through the lumen to the distal tip. In another variation, the probe further includes a $pO_2$ sensor and a temperature sensor. In one variation, the temperature sensor and $pO_2$ sensor utilize a single fiber optic.

Another variation of the present invention includes the multisensor probe as described above wherein the probe further includes a form of a 18-21 gauge needle. In one variation, the needle is blunt. In another variation the needle is sharp. In still another variation the needle is cut and polished at an angle less than 70 degrees and preferably ranging from 40 to 60 degrees.

Another variation of the present invention includes a multisensor probe for tissue identification. The probe is connected to a controller via a cable. The probe comprises a handle to manipulate the probe and a needle joined to the handle. A plurality of optical fibers extend from the controller, through the cable, through the lumen, to the distal tip of the needle. The probe also features a sheath slideably disposed around the distal section of the needle. The sheath is retractable into the handle when the distal section of the needle is inserted into the tissue. In this variation, the probe includes an optical position sensor coupled to the sheath to measure position of the retractable sheath relative to the handle.

Another variation of the present invention includes a multisensor probe for tissue identification. The probe includes a needle having a distal tip and a lumen extending through the needle to the distal tip and a plurality of optical fibers extending from the controller, through the cable, through the lumen, to the distal tip of the needle. In this variation, at least two of the plurality of optical fibers are optical scattering and absorption fiber optics and at least one of the plurality of optical fibers is an OCDR fiber optic. In a variation, the multisensor probe further comprises a linear optical encoder coupled to the needle to measure position of the distal tip relative to the tissue.

Another variation of the present invention includes a multisensor probe having a plurality of sensors configured as shown in any one of FIGS. 5A-5H. This variation may also feature a slideable sheath coaxially disposed over a distal section of the needle. The sheath is retractable from the distal section as the needle is inserted into the tissue. This variation also includes a position sensor configured to read the position of the sheath relative to the needle.

Another variation of the present invention includes a method for identifying tissue comprising manually inserting a multisensor probe as recited in any one of the above described probes.

Still another variation of the present invention is a tissue detection system comprising a multisensor needle comprising a plurality of optical fibers and a position sensor for determining position of the needle relative to the tissue. The system also includes a controller configured to deliver and collect light through the plurality of optical fibers wherein at least one of the fibers is utilized as an OCDR sensor and wherein at least one the optical fibers is utilized for optical scattering and absorption.

Additional aspects and features of the invention will be set forth in part in the description which follows, and in part will become apparent to those skilled in the art upon examination of the following or may be learned by practice of the invention.

DETAILED DESCRIPTION

The present invention includes a multisensor probe and system for identifying tissue such as cancerous tissue. The multisensor probe may be inserted into tissue and continuously measure a plurality of properties of the tissue while penetrating the tissue. A processing module may be provided to characterize the tissue based on information including but not limited to information received from the probe. The present invention may further include a graphical interface to conveniently display (in real time) results to a doctor while the doctor is inserting the probe into the tissue.

First Embodiment

Figure 1A:
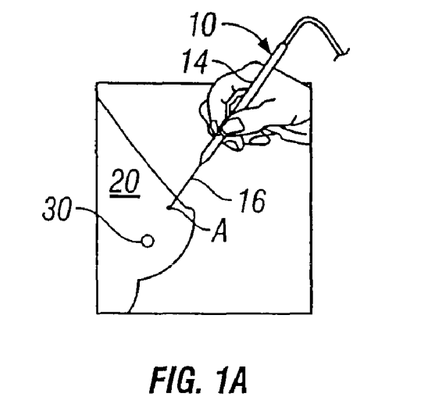
FIGS. 1A and 1B are illustrations of a multisensor probe in accordance with the present invention in an application.
Figure 1B:
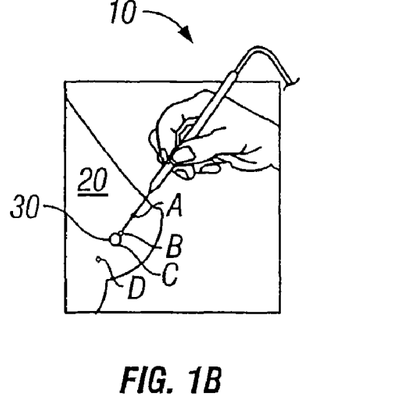
Figure 1C:
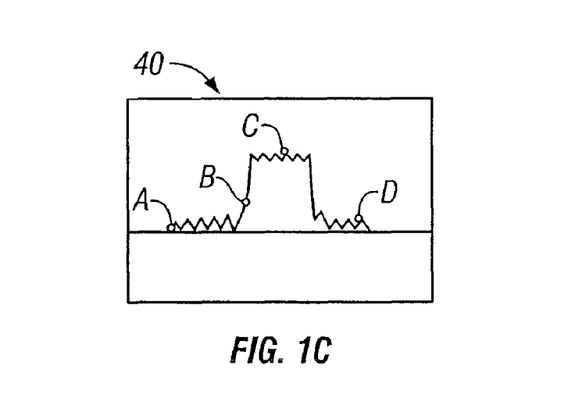
FIG. 1C is a graph of a tissue property versus position for the application illustrated in FIGS. 1A and 1B.

FIGS. 1A-1C illustrate an embodiment of the present invention in an application. Referring to FIG. 1A, a multisensor probe 10 is shown inserted in breast tissue 20. The multisensor probe 10 includes a handle 14 for manually manipulating the probe and a needle 16 extending from the handle. The distal tip of the needle is shown at location A and is directed towards a suspicious lesion 30. FIG. 1B shows the distal tip of the needle within the suspicious lesion 30 at location C.

The probe 10 includes a plurality of sensors to measure tissue properties which are useful in identifying tissue such as cancerous tissue. The sensors may take many forms including, for example, optical fibers for receiving and transmitting light to and from the probe tip. The probe's position or depth is also measured as the probe 10 is inserted into the tissue 20.

These measurements are preferably taken and processed continuously and in real time as the probe penetrates the tissue.

FIG. 1C shows graphical output 40 from the procedure illustrated in FIGS. 1A and 1B. In particular, graph 40 shows continuous measurement of a tissue property as a function of depth (or position). Location A corresponds to normal tissue; location B corresponds to a lesion boundary or margin; location C corresponds to the center of the lesion 30; and location D corresponds to normal tissue distal to lesion 30. A review of graphical output 40 enables a doctor to diagnose a suspicious lesion in breast tissue in real time.

Figure 2A:
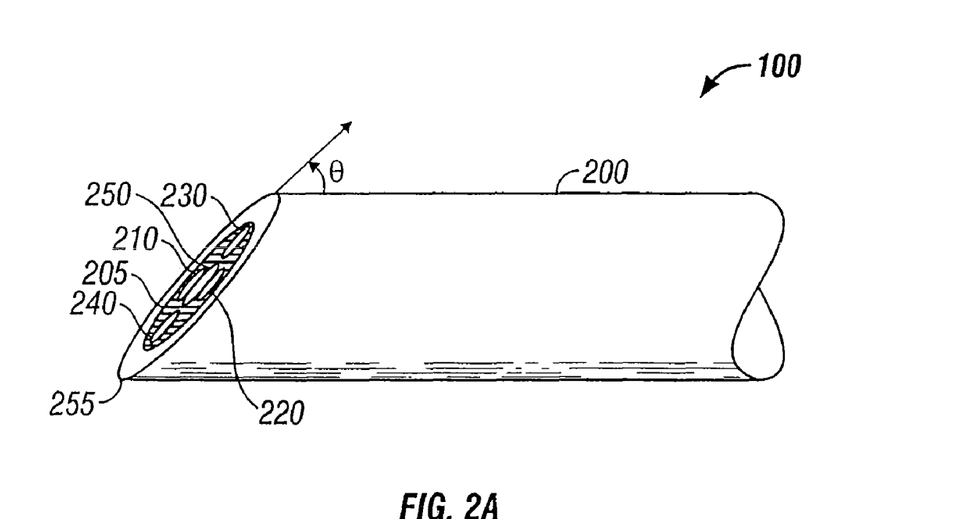
FIG. 2A is a partial perspective view of a distal section of a multisensor probe in accordance with the present invention.
Figure 2B:
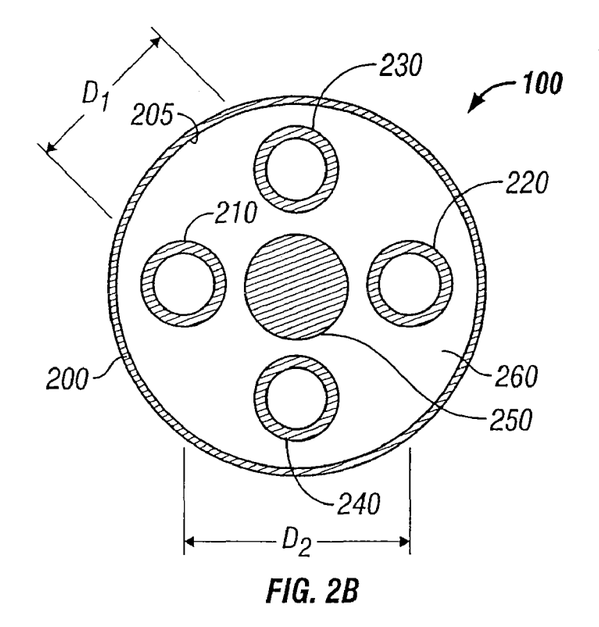
FIG. 2B is an end view of the multisensor probe shown in FIG. 2A.

FIGS. 2A and 2B show an enlarged view of a distal section of a probe in accordance with the present invention. Referring to FIG. 2A, probe 100 is shown having an elongate body 200 and a lumen 205 extending therethrough. A plurality of optical fibers extend through the lumen 205 to the distal end of the elongate body. Preferably, the optical fibers are flush with the distal end of the elongate body. It is preferred that the fibers or sensors contact or nearly contact the tissue as the probe penetrates tissue to be identified. Hereinafter, sensors include but are not limited to one or more optical fibers and conductors used for sensing.

The elongate body 200 may be, for example, an 18 to 21 gauge hypodermic type needle. The elongate body may have a length in the range of 0.5 to 20 cm., more preferably between 4 and 10 cm. Suitable materials for the elongate body are metals and plastics. A preferred material for the elongate body or needle is stainless steel. Suitable stainless steel tubing is available from Vita Needle, Needham, Mass. However, the elongate body 200 may be comprised of other materials and may have other sizes.

The needle 200 shown in FIG. 2A features a sharp distal end. The distal end is preferably cut and polished after the optical fibers and other sensors are positioned within the needle. Cutting the needle after the optical fibers are positioned within the needle allows the optical fibers to be cut flush with the distal tip of the needle. Preferably, the needle end is cut and polished at an angle θ less than 70 degrees, usually between 30 and 70 degrees and most preferably between 40 and 60 degrees. Angles less than 70 degrees are preferred because a sharp end more easily penetrates tissue. However, the distal end of the elongate body may also be blunt. Blunt tips may be suitable for penetrating soft tissue such as brain tissue.

The needle or elongate body may include outer markings which can be read or otherwise detected to determine the position or depth of the probe as it is inserted into tissue. Markings may be read by a camera or a technician examining the procedure. Suitable markings include but are not limited to bar code, magnetic codes, resistive codes, and any other code which can provide position information of a moving device.

FIG. 2B shows an end view of the needle 200 and is illustrative of one sensor configuration in accordance with the present invention. In particular, a conductor 250 is centrally positioned in lumen 205 and a plurality of optical fibers 210, 220, 230, 240 are shown circumferencially positioned about the conductor 250. The optical fibers may be single mode or multimode depending on their use, as will be discussed further below.

The optical fibers and conductor are preferably bonded within lumen 205 using a biocompatible compound such as, for example, F114 epoxy manufactured by TRA-CON, Inc. Bedford, Mass. Filling the lumen with a bonding compound prevents tissue from entering the needle tip as the probe is inserted into tissue.

Alternatively, the sensors may be molded or formed in the probe. For example, a biocompatible polymeric material may be coaxially formed around the individual sensors to form a solid polymer needle having the fiber optics bonded therein.

The optical fibers are also preferably coated with a reflective or metallic layer that prevents stray light from entering the fibers. A suitable coating is, for example, a 2000 A aluminum coating.

The optical fibers are used to measure tissue properties as the needle 200 is inserted into tissue. For example, optical fibers 210, 220, and 230 may be used as an optical scattering and absorption spectroscopy (OSAS) sensor and optical fiber 240 may be used as an optical coherence domain reflectometry (OCDR) sensor. While OCDR optical fiber 240 is shown at the apex 255 of the needle, the present invention is not so limited. For example, a fiber optic used in an OSAS sensor may be positioned at the apex 255 of the needle. For some applications, it may be desirable to have one fiber optic or wire positioned at the apex and consequently extend deeper into the tissue than the other sensors.

Optical Scattering and Absorption Spectroscopy

Optical fibers 210, 220 and 230 may be configured as an optical scattering and absorption spectroscopy (OSAS) sensor. It is to be understood that optical scattering and absorption spectroscopy includes various optical measurement techniques which use light scattering and absorption data to measure a target sample. Non-limiting examples of OSAS techniques include elastic scattering spectroscopy and inelastic scattering spectroscopy.

Figure 3:
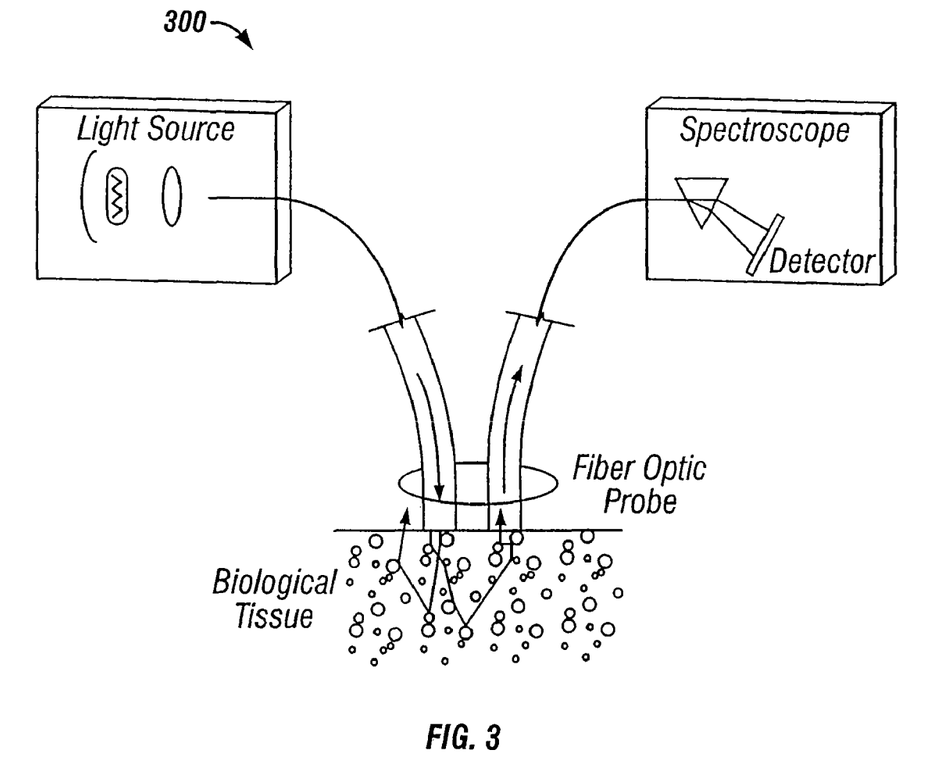
FIG. 3 is a schematic illustration of an optical scattering and absorption spectroscopy system in accordance with the present invention.

FIG. 3 is a schematic illustration of one exemplary optical scattering and absorption spectroscopy system. In the optical system shown in FIG. 3, two optical fibers within the probe needle are present for measurement of the scattered light: an illumination fiber to deliver light from one or more light sources to the tissue, and a collection fiber to receive the scattered photons from the tissue and deliver them to a detector. Light from the fiber at the probe tip enters the tissue and is absorbed and scattered. After multiple scattering events within the tissue, a fraction of the incident light enters the collection fiber, which is located near the illumination fiber. The collected light is transported by the fiber back to the instrument body where a grating spectrometer and CCD detector measures the scattered light intensity as a function of wavelength. This measured intensity can then be compared with the measured intensity for normal-tissue scattered light. Instead of using a grating and CCD detector, the scattered light may be measured with a series of detectors that use optical filters to separate the different light signals. If the light source includes multiple LED's or lasers then conventional modulation techniques can be employed to separate the different colors with electronic filters.

Each light source can provide light at a single wavelength (e.g., a laser), a narrow band wavelength (e.g., a LED), or a broad band wavelength (e.g., a xenon flash lamp) which is believed to be differentially absorbed by malignant tissue relative to normal or benign tissue. For example, it has been shown recently that some malignant breast tumors absorb relatively less light in the spectral range of 450-500 nm than normal breast tissue. See, for example, Bigio et al., *Diagnosis Of Breast Cancer Using Elastic-Scattering Spectroscopy: Preliminary Clinical Results*, Jour. Biomed. Optics 5, 221-228 (2000) and U.S. Pat. No. 5,303,026. Similarly, differential absorption in the region of 660 or 940 nm is indicative of deoxygenated hemoglobin, which is believed to be another indicator of malignancy.

The combination of three optical fibers (210, 220, and 230) as shown in FIG. 2B thus can estimate the optical absorption and scattering properties of tissue near the distal tip. In the configuration shown in FIG. 2B, optical fiber 210 may be a multimode optical fiber for emitting and collecting electromagnetic radiation typically in the spectral range of 200 nm to 2000 nm. Optical fibers 220 and 230 may also be multimode optical fibers for collecting light propagating through the tissue in the vicinity of the fibers. Fibers that can support multiple modes are preferred because they are easier to align and are more effective at collecting and transporting spatially incoherent light.

Note that the probe depicted in FIG. 2A shows OSAS light collecting fiber 230 extending to a point proximal to light collecting fiber 220. The present invention is not so limited and includes extending multiple light collecting or other optical fibers to identical or different points within the elongate body 200. A suitable configuration, for example, includes a first light collecting fiber extending to a first point along the needle and a second light collecting fiber extending to a second point wherein the first point is proximal to the second point from 100 to 700 um and more preferably from 100 to 400 um. Likewise, one or more light collecting fibers may extend to a point equal, proximal or distal to the tip of a light emitting fiber. When not extending to equal locations, the separation distances can be from 100 to 700 um and more preferably from 100 to 400 um. The above described fibers thus can extend to (and be flush with) the distal tip of an angled or "sharp" needle as well as a blunt needle. Staggering the optical fibers as described above may also increase the path length of photons traveling to the collecting fiber(s). This creates a longer mean free path and may make the instrument more sensitive to low concentrations where absorption is an important factor.

Note also the collecting fibers 220 and 230 are spaced apart in the radial direction from emitting fiber 210. A suitable (center to center) distance $D_1$ for light collecting fiber 230 to light emitting fiber 210 is from about 175 to 400 um. A suitable (center to center) distance $D_2$ for light collecting fiber 220 to light emitting fiber 210 is about 300 to 500 um. Of course, when using a needle having a larger inner diameter, fibers may be separated greater distances.

Optical Coherence Domain Reflectometry

The multisensor probe 100 of FIG. 2B also features an optical fiber 240 which can be used for performing optical coherence domain reflectometry (OCDR). OCDR is an optical technique which can be used to image 1-3 mm into highly scattering tissue. The technique may use a bright, low coherence source in conjunction with a Michelson interferometer to accurately measure backscattered (or transmitted) light as a function of depth into the media. A suitable interferometer is, for example, model 510 manufactured by Optiphase, Van Nuys, Calif.

Figure 4:
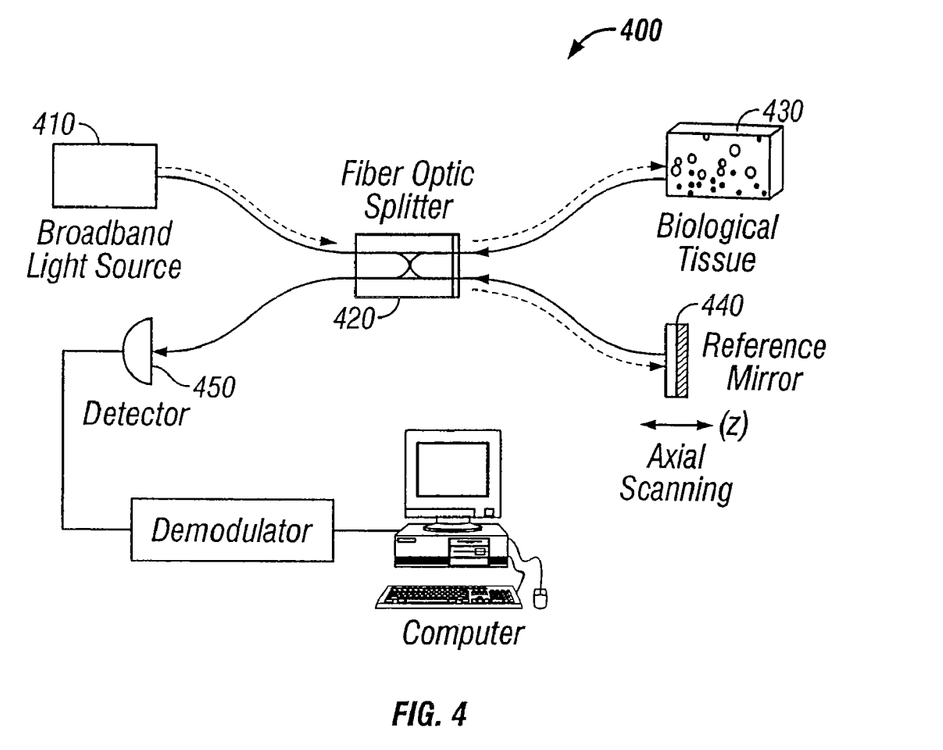
FIG. 4 is a schematic illustration of an OCT system in accordance with the present invention.

A schematic illustration of one OCDR system 400 which may be used with the present invention is shown in FIG. 4. Optical output from a low coherence super luminescent diode 410 is split in a fiber optic coupler 420 and directed toward the sample 430 and reference arms of the interferometer. Reflections from the reference mirror 440 and backscattered light from the sample are recombined at the splitter and propagated to the detector 450. Constructive interference at the detector produces a signal when the sample and reference optical path lengths are within the longitudinal coherence length of the optical source (typically <15 microns). The scanning mirror in the reference arm is used to scan the detection point within the sample thereby generating a single line scan analogous to the A-scan in ultrasound. This single line scan is sometimes referred to as optical coherence domain reflectometry (OCDR).

The fiber optic 240 used for OCDR is preferably a single mode fiber. A suitable inner diameter for the fiber optic 240 is 125 microns. An OCDR sensor can provide information about the optical properties of tissue along a single line defined by the optical fiber 240 cone of optical emission. The axial spatial resolution along this line is determined by the spatial coherence of the optical source and is typically less than 15 microns. The transverse spatial resolution is determined by the fiber optic and tissue index of refraction and can vary from five microns near the fiber tip to hundreds of microns several mm into the tissue.

In addition to single line scans as described above, a cross-sectional or optical coherence tomography (OCT) image is produced by scanning the optical fiber across the sample and collecting an axial scan at each location. OCT techniques are discussed in D. Huang, et al., *Optical Coherence Tomography*, Science 254, 1178 (1991) and Swanson, et al., Optics Letters 17, 151 (1992).

Other OCDR and OCT systems which can be used with the present invention are described in Colston et al., *Imaging Of Hard And Soft Tissue Structure In The Oral Cavity By Optical Coherence Tomography*, Appl. Optics 37, 3582 (1998); Sathyam et al., *Evaluation Of Optical Coherence Quantitation Of Analytes In Turbid Media Using Two Wavelengths*, Applied Optics, 38, 2097 (1999); and U.S. Pat. Nos. 5,459, 570; 6,175,669; and 6,179,611.

Electrical Impedance

Probe 100 depicted in FIGS. 2A and 2B additionally includes an electrical impedance sensor. Electrical impedance sensor in this embodiment includes electrically conducting elongate body 200 and conductor 250. Suitable materials for the elongate body in this configuration include electrically conducting metals as well as electrically conducting polymers. The distal tip of the elongate body 200 and conductor 250 contact the tissue when the probe is inserted into tissue. The impedance sensor can thus measure various electrical properties including electrical impedance of the tissue near the probe tip.

In a preferred embodiment the electrical impedance is measured at multiple frequencies that can range from 1 kHz to 4 MHz, and preferably at 5, 10, 50, 100, 200, 500, 1000 kHz. Electrical impedance is another measurement which is believed to be useful in characterizing tissue, especially when combined with other tissue properties.

In summary, FIGS. 2A and 2B illustrate a multisensor probe 100 having an OSAS sensor, an OCDR sensor, and an electrical impedance sensor in accordance with the present invention.

Other Sensor Configurations

The sensor configurations of the present invention may vary widely and may incorporate more or less sensors than those described above.

FIGS. 5A to 5H illustrate cross sectional views of a multisensor probe having various sensor configurations in accordance with the present invention. The configurations shown in these figures are exemplary and not intended to limit the present invention which is defined by the appended claims.

In each of FIGS. 5A-5H, the needle or elongate body 500 circumferentially surrounds a plurality of sensors including OSAS fiber optics 510; OCDR fiber optics 520; electrical impedance electrodes 530; $pO_2$ fiber optics 554; combination temperature and $pO_2$ fiber optics 550; temperature sensors 560; chemical sensors 570.

Figure 5A:
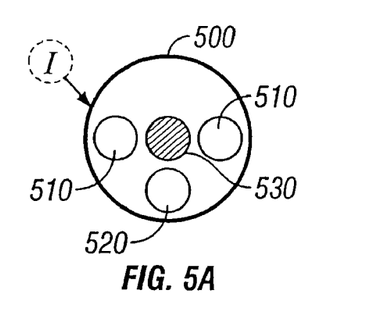
FIGS. 5A-5H are cross sectional views of various multisensor probes in accordance with the present invention.
Figure 5B:
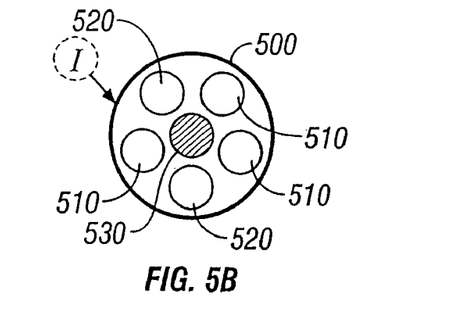
Figure 5C:
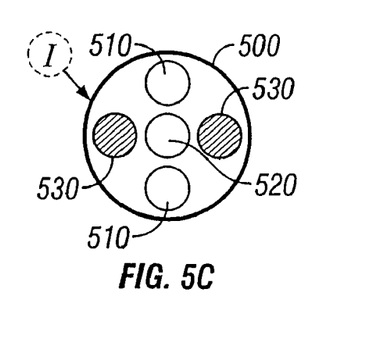

Referring to FIGS. 5A-5C, the needle includes one or more OSAS fiber optics 510, one or more OCDR fiber optics 520, and one or more electrical conductors 530 for measuring electrical properties such as electrical impedance. In each of FIGS. 5A-5C, the elongate body 500 is electrically conducting and also used as one of the conducting elements for the impedance sensor. Consequently, the electrical impedance sensor in FIG. 5C includes 3 conducting elements.

Figure 5D:
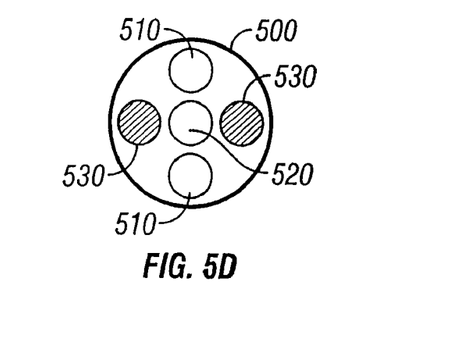

The probe illustrated in FIG. 5D is identical to that shown in FIG. 5C except that the elongate body 500 is not a conductor used in sensing electrical impedance. The elongate body 500 may be made of non-electrically conducting material in this configuration such as a polymeric material.

Figure 5E:
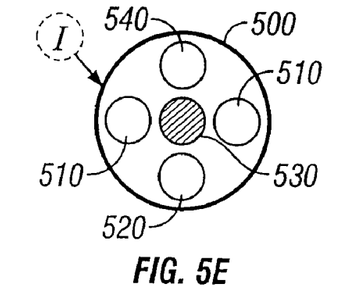
Figure 5F:
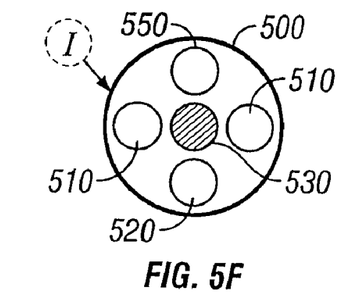
Figure 5G:
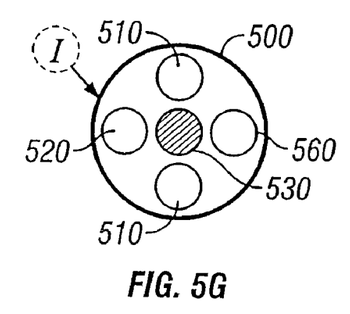

As shown in FIGS. 5E-5G, other sensors may be included within elongate body 500. The probes shown in FIGS. 5E-5G additionally include a $pO_2$ sensor 540, a temperature/$pO_2$ sensor 550, and temperature sensor 560 respectively.

Temperature and $pO_2$ measurements are believed to be useful in identifying abnormal tissue. Malignant tumors are frequently characterized by reduced $pO_2$ and elevated temperature levels relative to adjacent normal tissue or benign tumors. One convenient all-optical way to measure $pO_2$ is by means of fluorescence of a dye that is quenched by the presence of oxygen. In this approach, the tip of an optical fiber contained within a probe needle is coated with a thin layer of an appropriate fluorescent material. The tip of the fiber is at the tip of the needle, and is in direct contact with the tissue. The fluorescent material is excited by means of, for example, a blue LED located in the instrument body at the proximal end of the fiber and, for example, a red fluorescent light emitted by the material is collected by the fiber and returned to the proximal end of the fiber where it is spectrally or otherwise separated from the excitation light. The fluorescence lifetime of the dye depends inversely on the amount of oxygen that diffuses into the material from the surrounding tissue.

The lifetime can be accurately measured by a technique in which the excitation light is modulated at a convenient frequency and the phase of the fluorescence signal is measured relative to the phase of excitation. See Hoist et al., *A Microoptode Array For Fine-Scale Measurements Of Oxygen Distribution*, Sensors and Actuators B 38-39, 122-129 (1997). Since the phase of the fluorescence signal depends on the lifetime, the phase measurement provides a convenient way to measure $pO_2$ that is not affected by coating uniformity or fiber transmission losses. Suitable oxygen sensors which may be incorporated into the present invention are, for example, fiber optic oxygen microsensors manufactured by PreSens, GmbH.

Temperature may also be measured by an all-optical technique that is essentially identical to the method used to measure $pO_2$. See Klimant et al., *Optical Measurement Of Oxygen And Temperature In Microscale: Strategies And Biological Applications*, Sensors and Actuators B 00 1-9 (1996). In the case of temperature, a different fluorescent material whose lifetime is related to temperature is coated on the fiber tip. A phase-fluorescence detection scheme similar to the phase-fluorescence detection scheme for detecting oxygen can be used for the temperature detection sensor with, perhaps, a different excitation wavelength and a different modulation frequency.

The temperature and oxygen sensors may be incorporated into one optical fiber. This is illustrated in the probe shown in FIG. 5G. The combined oxygen and temperature sensor 560 could have, for example, a tip coated with two dyes: one dye corresponding to the oxygen and one dye corresponding to the temperature. The other aspects of the temperature and oxygen detection would be similar to the detection and processing techniques described above.

The multisensor probes depicted in FIGS. 5E-5G also include an OSAS sensor 510, and OCDR sensor 520, and an impedance sensor 530. In FIGS. 5E-5G, the elongate body 500 is electrically conducting and used as one of the conductors in an electrical impedance sensor.

Figure 5H:
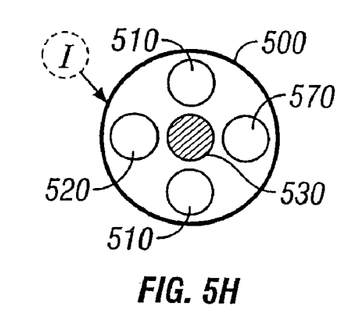

FIG. 5H illustrates yet another sensor configuration having a chemical sensor. Suitable chemical sensors may include materials (e.g., catalyst) which react to the tissue being penetrated and ion sensors. The multisensor probe of FIG. 5H also includes an OSAS sensor 510, an OCDR sensor 520, and an impedance sensor 530. The elongate body acts as a second conductor element for the impedance sensor.

While not shown, other sensors may be incorporated into the elongate body 500 such as stiffness/elasticity sensors, fluorescence sensors, velocity and accelerometer sensors, pressure transducer or tube sensors, and any other sensor or tool so long as it may fit within the lumen of the elongate body.

Second Embodiment

Figure 6:
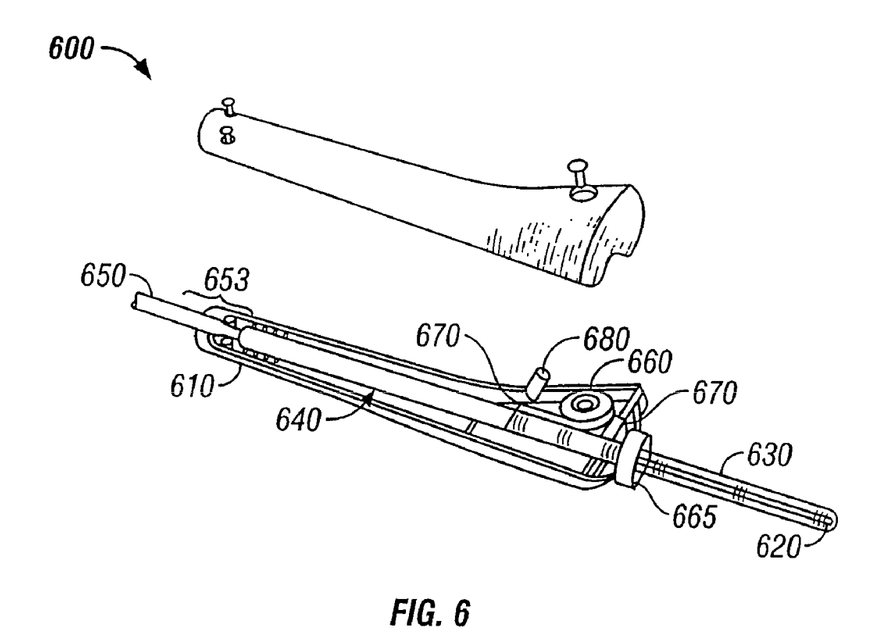
FIG. 6 shows an exploded view of a multisensor probe in accordance with the present invention.

Another multisensor probe 600 in accordance with the present invention is shown in FIG. 6. The multisensor probe 600 includes a handle 610 and an elongate body or needle 620 extending from the distal end of the handle. The needle 620 is shown within a slideable sheath 630.

Sheath 630 is configured such that it retracts into the handle 610 when the needle is inserted into tissue. When not retracted, the slideable sheath 630 covers the needle 620 to protect against accidental needle exposure. The sheath 630 is urged over the needle using a resilient member 660 such as a spring. The spring connects to the sheath and applies a force urging the sheath over the full length of the needle. The force supplied by the resilient member 660, however, is not so great that it inhibits manipulation of the needle into the tissue. The resilient member is thus selected or adjusted to allow the sheath to easily retract as the needle is inserted into tissue. Suitable materials for the sheath include polymeric materials, preferably hard.

The multisensor probe 600 may also include a locking member such as a locking ring 665. The locking ring 665 may be set such that movement of the sheath is prevented until the locking ring is rotated. Locking the sheath over the needle is helpful to prevent accidental needle exposure.

The multisensor probe shown in FIG. 6 features a shaft 640 inside the handle 610. The shaft is affixed within the handle and provides a surface for the sheath to slide over when the sheath retracts into the handle. The shaft may coaxially surround the fiber optics, conductors and any other sensors to be used in the multisensor probe. The needle 620 is aligned and attached to the shaft such that the needle extends from the handle. The sensors and optics within the shaft continue through the shaft and into the needle. The sensor configurations may be similar to the sensor configurations described above.

The fiber optic, electrical conductors and other sensors may connect to a controller (not shown) which drives the sensors and receives signals from the sensors. The sensor optics and wiring may extend from the handle to the processor within a flexible cable 650. The flexible cable 650 holds and provides protection to the sensors.

The flexible cable includes a proximal end (not shown) and a distal end 653. The distal end of the cable 650 is joined to the proximal end of the probe handle. In particular, FIG. 6 shows the distal end of the cable joined to the proximal end of shaft 640. While not shown, resilient members or connectors may be deployed at the proximal end of the probe handle (i.e., the interface between the cable to the handle) to prevent bending moments from damaging the sensors within the cable.

The proximal end of the cable 650 (not shown) preferably terminates at a optical connector or coupling. The coupling can be removably connected to the processor. The connector, for example, may be similar to a fiber optic ST connector. Thus, the multisensor probe and flexible cable may be easily connected to the processor prior to a procedure and removed from the processor following the procedure. The multisensor probe 600 is, in this sense, disposable after a use.

A memory device may also be incorporated into the probe or the connector section of cable 650. The memory device could contain information about the probe including calibration parameters. Calibration parameters are useful for data analysis. In addition, the memory device can be used to detect and prevent multiple uses of the device. A suitable memory device that can be integrated with the control electronics is GemWave™ C220 available from GEMPLUS.

Position Sensor

The multisensor probe shown in FIG. 6 also includes a position sensor 670. The position sensor 670 can be an optical position sensor that measures light reflected off an encoded surface of the sheath 630. Alternatively, the position sensor 670 could be a resistive or capacitive sensor that couples to a conductor within the sheath 630.

Also, position sensor 670 can be a fiber optic that delivers light from an external light source onto the sheath 630 and returns the reflected light back to an external detector. The external light source could have multiple wavelengths (e.g. red and green); a color-coded pattern on the sheath having at least three different colors would allow for detecting a change in position and direction (e.g. red, green, black).

Figure 7:
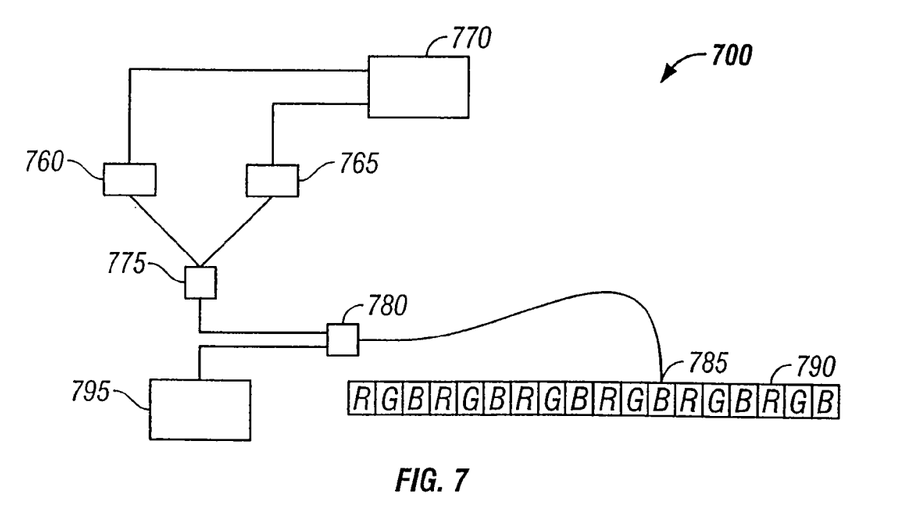
FIG. 7 is a schematic illustration of a position sensor system in accordance with the present invention.

FIG. 7 is a schematic of an optical position sensing system 700 in accordance with the present invention. In FIG. 7, two colored light emitting diodes (LEDs) 760 and 765 are powered by a power supply 770. The power supply 770 may, for example, modulate LEDs 760 and 765 at two different frequencies to allow electronic separation of the two colors.

Light from the LEDs 760 and 765 is combined at fiber optic splitter 775. The light then propagates through a second fiber optic splitter 780 to fiber tip 785 where the light exits. The light emitted from the fiber tip 785 reflects off color coded bar 790 and returns through the splitter 780 to the optical detector 795.

Coded bar or encoder 790 may have various configurations. In one variation, the color bar 790 has a repeated three-color pattern (e.g., red, green, blue). As the color bar 790 moves past the fiber tip 785 the relative amplitude of the two colors is decoded to determine the bar color. By counting the number of bars and the direction the control electronics can keep track of the bar position relative to the initial starting point. The direction is calculated by noting the sequence of color bars. In another variation, color bar 790 has a continuous transition between two different colors that each correspond to a signal maximum for each LED color. The absolute position along the bar can be determined from the relative intensity of each LED 760 and 765 of the optical detector 795.

In another optical sensor in accordance with the present invention, only one color LED is used and the color bar is selected to produce at least three reflected intensity levels. This approach may work with a continuous and a noncontinuous transition between the color bars. However, this approach may be more susceptible to noise than using multiple LEDs.

The above mentioned optical position sensors are described in connection with a sheath 630 or like component. When the sheath or other component is retracted as the needle is inserted, an encoder on the sheath moves relative to a detection point on the handle of the multisensor probe. However, the present invention is not limited to the above noted position sensors. Any suitable position sensor may be used and incorporated with the multisensor probe of the present invention. For example, the depth of the needle may be measured using a form of ranging technology wherein a laser beam is emitted from the handle 610 to the tissue surface. For example, the position of the handle relative to the tissue surface may be determined based on the reflected signal of the laser beam. Sonic and ultrasonic sensors may also be employed to determine the position or depth of insertion of the needle.

Another position sensor in accordance with the present invention is to provide visual marks on the needle. A person watching the procedure could record the number of marks remaining outside the surface as the needle is inserted into the tissue. Or, a person may record the number of marks on the needle covered by tissue as the needle is inserted into the tissue. A camera may be provided to image the marked needle as it is pushed into tissue. Image analysis would provide depth as a function of time. However, one disadvantage of position sensors using ranging or imaging techniques is that the user would have to avoid blocking the sensor or camera.

Selected positions may be identified by pressing a button or switch 680 of FIG. 6. When activated (e.g., pressed), the button would identify or mark selected positions during insertion of the probe. For example, the physician may press a switch or button when the needle probe hits a suspect lesion boundary. The selected position is marked and its location can be used later by analysis software to distinguish normal tissue from suspicious tissue. Suitable forms of markers include but are not limited to a lever, button, voice recognition or foot switch.

Tissue Identification Systems

The multisensor probe of the present invention may be used in conjunction with various tissue identification systems. Typically, a tissue identification system would include a multisensor needle probe, a control module and a flexible cable that connects the probe to the control module. The control module typically includes electromagnetic radiation sources, optical detectors, electrical impedance measurement electronics, and control electronics. Computer software may analyze data collected during the procedure (e.g., continuously and in real time) and then provide information about the tissue type.

Figure 8:
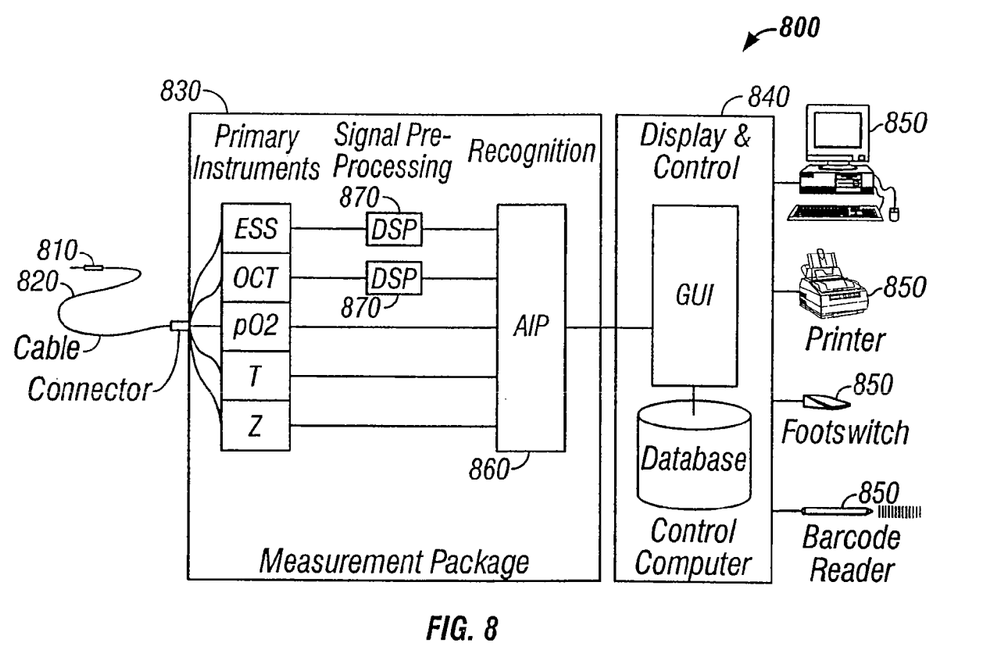
FIG. 8 is a schematic illustration of a multisensor system in accordance with the present invention.

A tissue identification system 800 in accordance with the present invention is illustrated in FIG. 8. The system 800 includes a multisensor probe 810, a cable 820, a measurement package 830, a computer 840, and various I/O devices 850 connected to the computer.

The measurement package 830 drives various sensors of the probe and measures their responses. As discussed above, there may be five sensors to the measurement package including: an optical scattering and absorption spectroscopy instrument; an Optical Coherence Domain Reflectometry instrument (OCDR); an Oxygen Partial Pressure instrument ($pO_2$); a temperature measurement instrument (T); an electrical impedance measurement instrument (Z). The measurement package may additionally feature, but need not to, an Artificial Intelligence—Pattern Recognizer Engine (AIP) 860.

Digital Signal Processors (DSP) 870 can be used to control and pre-process signals which are then fed into the Artificial Intelligence—Pattern Recognizer Engine (AIP) along with the other signals. The AIP 860 may be a specialized processor to perform pattern matching on the data received from the other components of the instrument package. Both artificial neural networks and hierarchical cluster analysis can be employed to classify the data against other data sets such as data sets generated during, for example, clinical trials. Data can also be compared to normal tissue samples at another location within the patient.

The electronics and processor are preferably configured to take measurements continuously and in real time. Preferably, the electronics and processor are configured to take measurements of the tissue every 1 mm for an needle insertion speed of 1 cm/s and more preferably, every 0.2 mm. This corresponds to sampling rate of at least about 10 Hz and 50 Hz respectively. The above sampling rate provides for determining tissue structure on a microscopic and macroscopic scale (i.e., 10 micron to 10 centimeters).

The Control Computer 840 can provide a convenient human interface and data management system. It may include, for example, various input/output (I/O) devices such as but not limited to: a graphics display for presenting data in real time, and prompting the operator for inputs; a keyboard for the operator to control the system and input information; a speaker for audible feedback; a microphone for the operator to annotate readings; a foot switch for the operator to tell the system to "tag" or mark specific data points; a printer for hard copy results; a bar code scanner for inputting patient ID; and a communication port to interface with hospital or laboratory information systems and internet.

Figure 9:
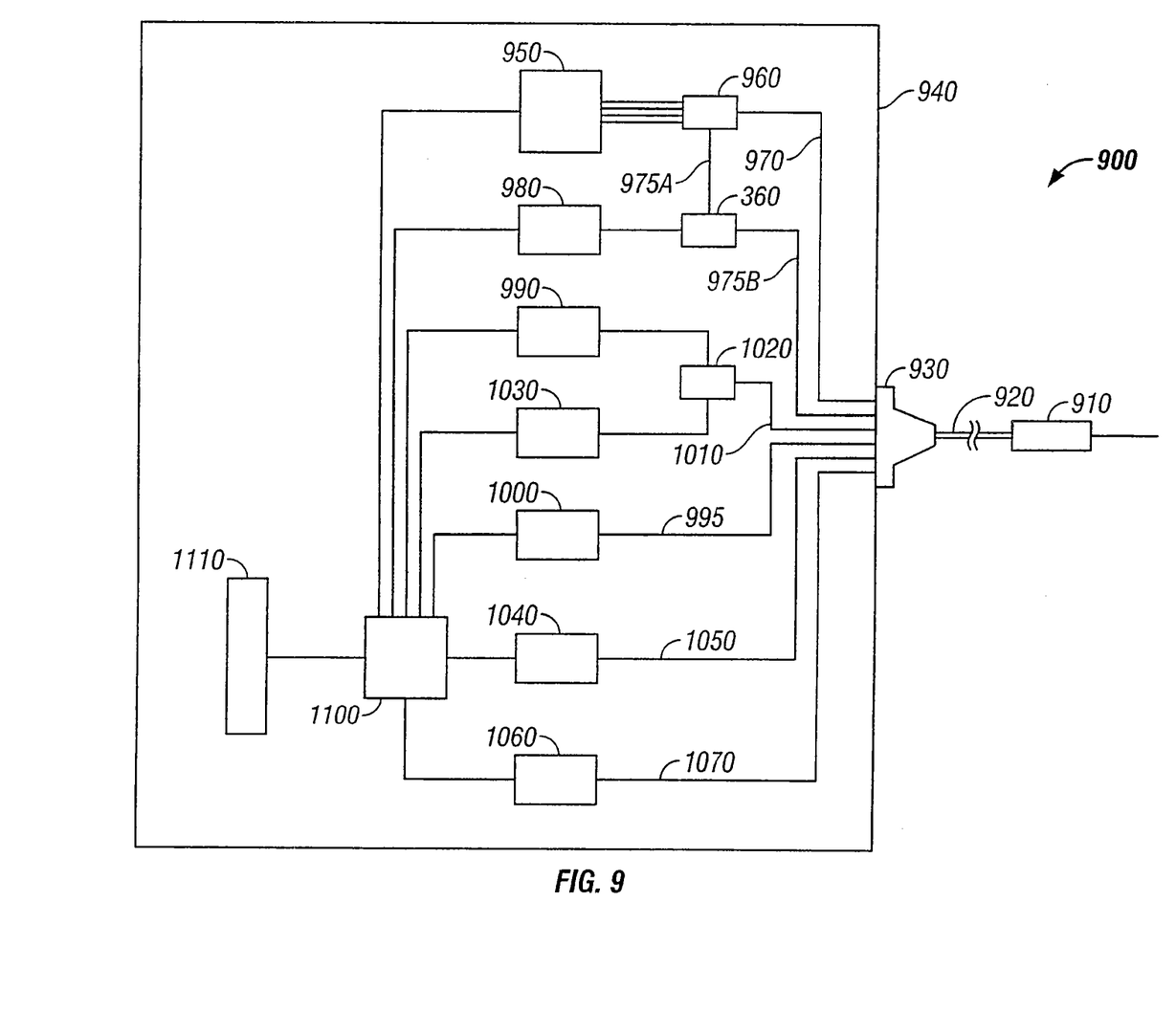
FIG. 9 is a schematic illustration of a multisensor system having a reference optical fiber.

FIG. 9 shows a schematic of another tissue identification system 900 in accordance with the present invention. The system 900 includes a multisensor probe 910, a cable 920 that connects the probe to a connector 930 located on the control module 940. The control module 940 includes electromagnetic radiation sources 950 which may be, for example, multiple lasers or white light sources (e.g. "X-strobe" sold by Perkin Elmer Optoelectronics, Inc. Salem, Mass.).

A fiber optic splitter 960 splits light from sources 950 into an emission fiber 970 and a reference fiber 975A. In this embodiment, a reference fiber 975B goes to the probe and returns to a detector 980. The reference fiber 975B preferably extends into the handle of the probe and not into the needle.

By measuring signals of the reference fiber, fluctuations in light delivery to the tip of the device due to cable motion may be partly accounted for. Fluctuations may occur for a variety of reasons including losses through the fiber due to bends in the fiber. Each of the optical fibers in the probe likely experience similar losses as the reference fiber. This assumption is more accurate if the fibers have a similar numerical aperture, material properties and are tightly packed and possibly bonded within the cable. The fibers can be bonded using a soft polymer compound or silicone.

The detection system shown in FIG. 9 features an OSAS sensor and light is delivered to the sample via fiber 970. Light is collected by two collection fibers 995, 1010 and is delivered from the connector 930 to separate optical detectors 990, 1000.

Additionally, light from collection fiber 1010 is split at splitter 1020 to deliver light to a fluorescence optical detector 1030. The fluorescence detector 1030 may be filtered with, for example, notch filters (available from CVI Laser corp. Albuquerque, N. Mex.) to block out the excitation laser light.

Optical detectors within the control module can be a grating spectrometer (e.g. S2000 fiber optic spectrometer, sold by Ocean Optics Inc., Dunedin, Fla.). Alternatively, the light sources may be modulated (e.g. PMA Laser Diode Modules, supplied by Power Technology Inc., Little Rock, Ark.) and electronic filters can be used to measure the optical signal at each modulation frequency which is different for each wavelength. When the light sources are modulated, an optical detector can be a silicon photo detector (e.g. PDA55, supplied by ThorLabs Inc. Newton, N.J.).

The tissue identification system 900 may also include an OCDR sensor. The OCDR sensor preferably includes an optical fiber extending to the distal tip of the needle probe 910. Additionally, the control module preferably features an OCDR light source, detector and measurement electronics 1040 (e.g. OCDR system available from OptiPhase Inc., Van Nuys, Calif.). The OCDR fiber 1050 is used to both deliver and collect light from the needle probe 910.

The tissue identification system 900 shown in FIG. 9 also features an electrical impedance sensor. The electrical impedance sensor operates with an electronics module 1060 and may include a three-conductor cable 1070 extending to the distal tip of the probe 910.

A main electronics control module 1100 may power and control the various components and acquire data from the detectors. Analysis software may process the data and displays results on display 1110. A variety of analysis techniques can be applied including, for example, neural networks as described in U.S. Pat. No. 6,109,270 to Mah et al. and hierarchical (and nonhierarchical) cluster analysis as described, for example, in papers by I. J. Bigio, et al, "Diagnosis of breast cancer using elastic-scattering spectroscopy: preliminary clinical results" in Journal of Biomedical Optics, 5(2), 221-228, (April 2000) and Multivariate Data Analysis, Fifth Edition, by Hair, et al, (1998).

A preferred algorithm includes comparing measurements from normal tissue to measurements of a suspect tissue area. This can be carried out in real time as the probe is inserted. In particular, tissue proximal to the target tissue provides a baseline value to the suspect tissue. For example, when inserting the probe into the breast to identify suspect tissue, the needle is inserted into the breast in a direction towards the suspect tissue. The breast tissue penetrated proximal to the suspect tissue may be used as a baseline to compare to measurements of the suspect tissue.

Another procedure includes comparing probe measurements of the suspect or target tissue to probe measurements taken from another body location. For example, the probe may be inserted into left breast tissue to provide a baseline. The probe may then be inserted into the right breast having the suspect lesion. Comparison of the baseline to the suspect tissue indicates whether the suspect tissue is normal.

Additional information may be used in an analysis to identify the suspect tissue. Additional information (e.g., patient history) may be used to weight or affect measured values to make the diagnosis more accurate. Further, any combination of useful algorithms may be employed with tissue identification system of the present invention so long as one algorithm does not exclude use of another algorithm. Non limiting examples of other algorithms include but are not limited to multiple regression analysis, multiple discriminant analysis and multi-variable pattern recognition.

Figure 10:
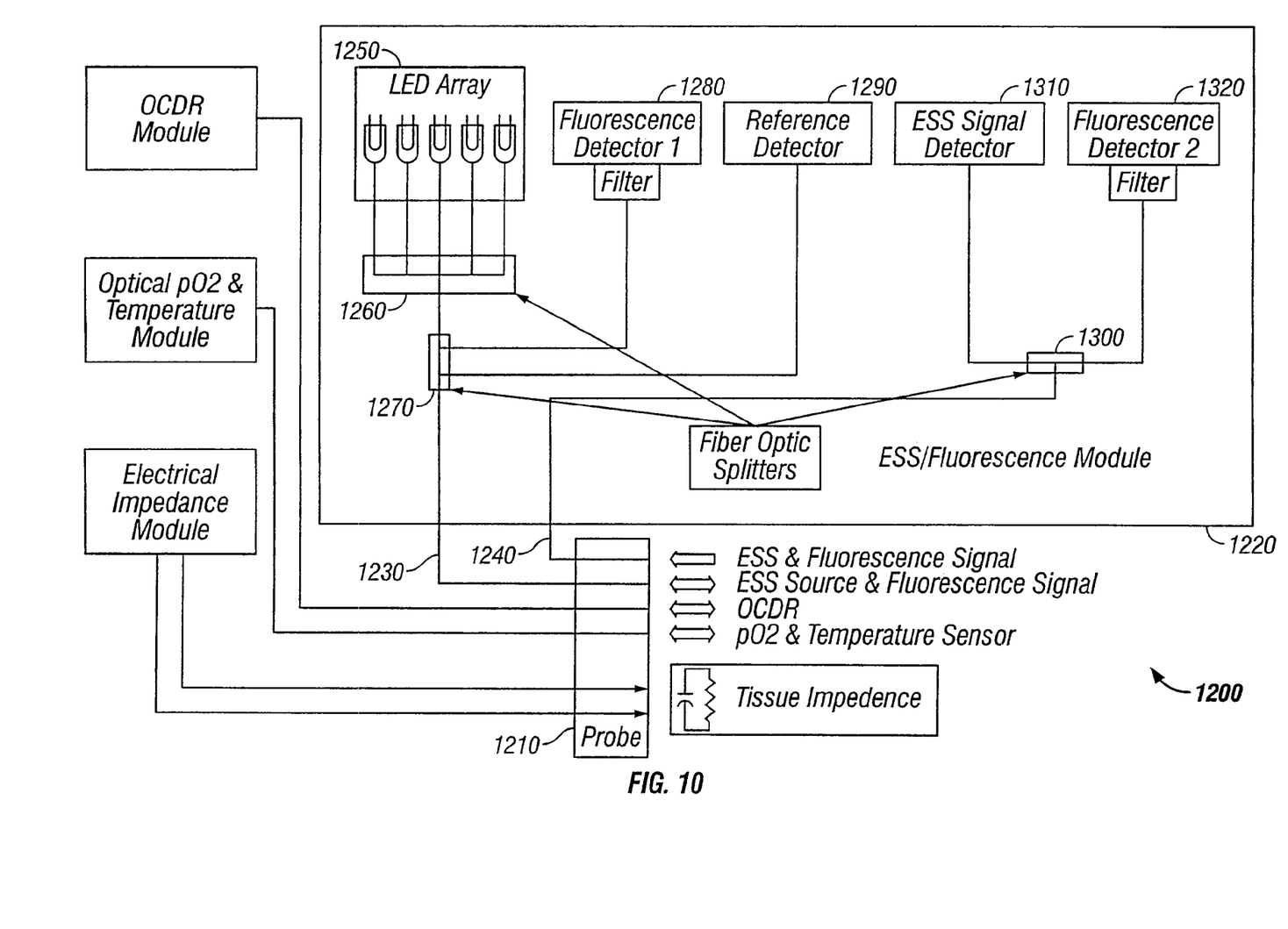
FIG. 10 is another schematic illustration of a system in accordance with the present invention.

FIG. 10 shows a schematic of another tissue identification system 1200 in accordance with the present invention. The system 1200 includes a multisensor probe 1210 coupled to four sensor modules which could be housed in a single control unit module (not shown). In particular, the system 1200 includes an OCDR sensor, an optical $pO_2$ and temperature sensor, an electrical impedance sensor, and an OSAS sensor. The OCDR sensor, an optical $pO_2$ and temperature sensor and electrical impedance sensor may be configured similar to the sensors described above.

The OSAS sensor includes a control module 1220, a light emitting fiber 1230, and a light collecting fiber 1240. The control module 1220 includes electromagnetic radiation sources 1250 which may be, for example, multiple LEDs (e.g., five different wavelength LEDs), white light sources, or lasers. Light emitted from radiation sources 1250 is coupled into one fiber at first splitter 1260. The light is delivered from first splitter 1260 to a second splitter 1270 where it splits into two optical fibers. One fiber leads to reference detector 1290, and one fiber leads to the sample via emitting source fiber 1230. Back scattered and fluorescence generated at the tissue returns through fiber 1230 and at splitter 1270 couples into a fiber that leads to fluorescence detector 1280. The light delivered to the fluorescence detector 1280 may be filtered with, for example, notch filters (available from CVI Laser Corp., Albuquerque, N. Mex.) to block out the excitation laser light.

Light delivered to the sample reflects, transmits and is absorbed by the sample. A collection fiber 1240 collects radiation from the sample. Light collected in the collector fiber 1240 is then delivered to a third optic splitter 1300 which splits the light into two optics. One optic delivers light to a first detector 1310 which measures, for example, an OSAS signal and one optic delivers light to a second detector 1320 which includes a filter to measure fluorescence. The light delivered to the fluorescence detector 1320 may be filtered with, for example, notch filters (available from CVI Laser corp. Albuquerque, N. Mex.) to block out the excitation laser light.

APPLICATIONS

Applications for the present invention can vary widely. For example, the present invention may be used to detect cancerous tissue in the breast. The multisensor probe of the present invention may also be used to characterize other types of abnormalities found in other locations of the body. The probe of the present invention may be used in vivo as described above or alternatively, the probe may be used to identify tissue in vitro. Preferably, the probe of the present invention is configured to measure tissue properties in real-time and continuously as the probe tip is inserted into a tissue sample. The probe of the present invention is thus effective beneath the surface of an organ or tissue sample (e.g., subcutaneously) and is not limited to merely contacting a surface or surface area of tissue to be diagnosed. While penetrating the tissue sample, signals from the multiple sensors of the probe are immediately processed to quickly diagnosis, identify or characterize the tissue.

The device of the present invention may also be used in combination with other medical devices. For example, the needle of the multisensor probe may be inserted through a cannula or other tubular structure used in medical procedures.

The present invention also includes a method and device for determining the approximate size of an abnormality such as a tumor. The size of the tumor could be calculated based on marking the boundaries of the suspicious lesion as discussed above. The distance between the first and second boundary could be stored and used in an algorithm to determine an approximate size of the suspicious lesion.

Examples

A multisensor probe in accordance with the present invention was built and tested. The probe featured a needle, a handle for manipulating the handle, an OSAS sensor, and OCDR sensor, and an impedance sensor. The OSAS sensor included a source fiber and two collection fibers. The OCDR sensor included a single mode fiber. The electrical impedance sensor included a central conductor as one electrode and the outer needle wall as the second electrode.

Figure 11A:
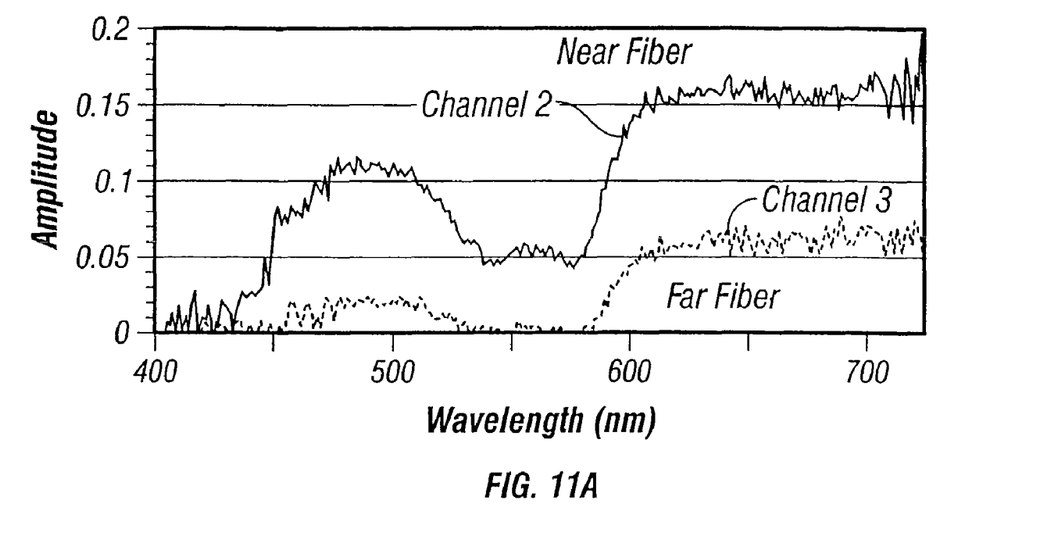
FIGS. 11A and 11B are measured spectra for normal and malignant tissue respectively using a probe in accordance with the present invention.
Figure 11B:
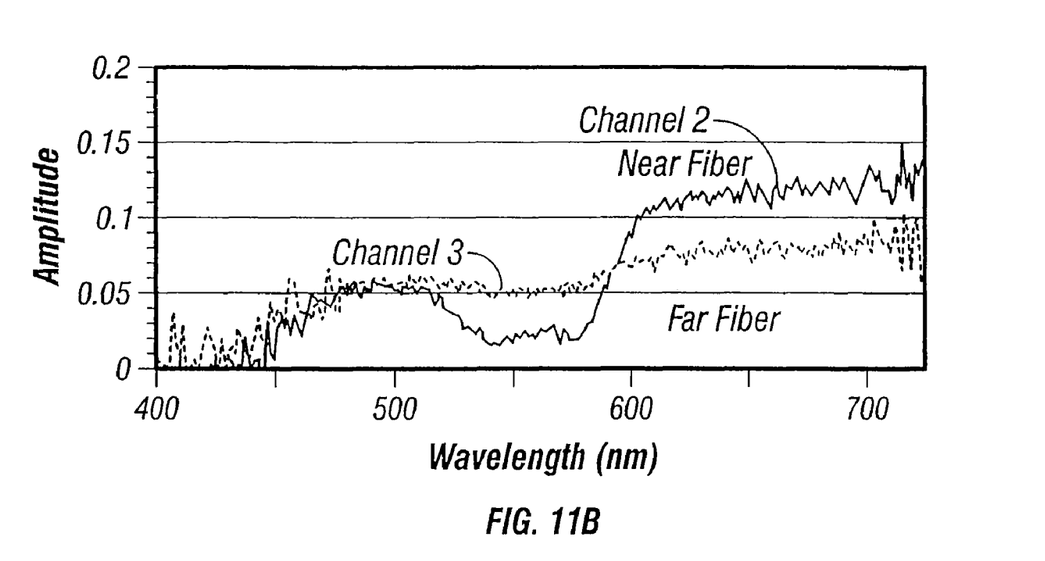

A xenon flash lamp was used as a light source for the test probe. FIGS. 11A and 11B show the spectrum of light collected by two OSAS fibers during in-vitro testing for normal and malignant tissue respectively. The line or "signature" represented by "channel 2" represents light collected from one optical fiber and the line represented by "channel 3" represents light collected from another optical fiber. The "channel 2" optical fiber was closer (center to center) to the light emitting fiber than the "channel 3" fiber.

Amplitude as a function of lambda (nm) is plotted in FIGS. 11A and 11B. As evidenced by the data, significant differences in tissue optical properties between normal and malignant tissue are observed. In particular, data corresponding to the malignant tissue (FIG. 11B) differs significantly from the data corresponding to the normal tissue (FIG. 11A). The differences include but are not limited to the amplitude as well as the slope of the amplitude. Further, the data lines differ at various wavelength ranges such as, for example, from 450 to 550 nm. Accordingly, the test probe of the present invention may be used to detect or differentiate malignant tissue from normal tissue.

All publications, patent applications, patents, and other references mentioned hereinafter are incorporated by reference in their entirety. To the extent there is a conflict in a meaning of a term, or otherwise, the present application will control.

All of the features disclosed in the specification (including any accompanying claims, abstract and drawings), and/or all of the steps of any method or process disclosed, may be combined in any combination, except combinations where at least some of such features and/or steps are mutually exclusive. Each feature disclosed, in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A multisensor probe for tissue identification, the probe connectable to a controller via a cable, the probe comprising:
   a handle;
   an elongate body having a distal tip and a lumen extending through the elongate body to the distal tip;
   a slideable sheath disposed over a distal section of the elongate body and being retractable from the elongate body toward the handle;
   a resilient member configured to bias the sheath toward the distal tip of the elongate body; and
   a plurality of optical fibers extending from the controller, through the cable, through the lumen, to the distal tip of the elongate body when the probe is connected to the controller, wherein at least two of the plurality of optical fibers are optical scattering and absorption spectroscopy fiber optics and wherein at least one of the plurality of optical fibers is an optical coherence domain reflectometry fiber optic, and wherein a position sensor is incorporated into the probe, the position sensor adapted to measure a depth to which the elongate body is inserted into tissue, the position sensor configured to read a position of the sheath relative to the elongate body.

2. The multisensor probe of claim 1 wherein the position sensor is a sensor selected from the group consisting of a resistive sensor and a linear optical encoder.

3. The multisensor probe of claim 1 having a conducting element extending through the lumen.

4. The multisensory probe of claim 1, further comprising a marking switch to identify a location in the tissue the distal section of the elongate body is inserted into the tissue.

5. The multisensory probe of claim 1, wherein the resilient member is a spring.

6. A tissue detection system comprising:
   a probe, the probe comprising a multisensor needle comprising a plurality of optical fibers, the probe further comprising:
      a handle;
      a slideable sheath disposed over a distal section of the needle and being retractable from the needle toward the handle;
      a resilient member configured to bias the sheath over the distal section of the needle;
      a position sensor adapted to sense depth of the needle inserted into tissue using the sheath wherein the sensor reads a position of the sheath relative to the needle; and
   a controller configured to deliver and collect light through the plurality of optical fibers wherein at least one of the plurality of optical fibers is utilized as an optical coherence domain reflectometry sensor configured for measuring backscattered and reflected light as a function of depth into the tissue and wherein at least one the optical fibers is utilized for optical scattering and absorption spectroscopy.

7. The system of claim 6 further comprising at least one electrode for sensing electrical information about the tissue.

8. The system of claim 6 wherein the sheath retracts when the needle is inserted into the tissue.

9. The system of claim 6, wherein at least two of the plurality of optical fibers are utilized for optical scattering and absorption spectroscopy, comprising a first light collecting fiber extending to a first point and a second light collecting fiber extending to a second point, wherein the first point is proximal to the second point.

10. The system of claim 9, wherein the first point is proximal to the second point by distance in the range of about 100 to about 700 µm.

11. The system of claim 6, wherein the plurality of optical fibers comprises a light collecting fiber having a center and a light emitting fiber having a center wherein the center of the light collecting fiber is separated from the center of the light emitting fiber by 175 to 500 µm.

12. The system of claim 6, wherein the probe further comprises a marking switch to identify a location in the tissue the distal section of the needle is inserted into the tissue.

13. The system of claim 6, wherein the resilient member is a spring.

14. The system of claim 6, wherein the controller is configured to indicate tissue abnormalities by comparing measurements from the plurality of optical fibers in real-time to prior measurements from the plurality of optical fibers obtained from a sample measurement session.

15. A diagnostic method, comprising:
   penetrating a skin surface with a sharp tip of a multisensor probe, wherein the skin surface retracts a sheath away from the sharp tip and toward a probe handle as the probe is inserted;
   continuously measuring the position of the sheath relative to the probe handle while the skin surface is penetrated using a position sensor that reads the position of the sheath;
   continuously delivering and sampling light from a plurality of optic fibers;
   performing optical scattering and absorption spectroscopy adjacent to the skin surface using at least one of the plurality of optic fibers and obtaining optical scattering and absorption spectroscopy measurements;
   performing optical coherence domain reflectometry adjacent to the skin surface using at least one of the plurality of optic fibers and obtaining optical coherence domain reflectometry measurements;
   repositioning the distal tip of the multisensory probe from the skin surface to a suspect tissue region;
   performing optical scattering and absorption spectroscopy at the suspect tissue region using at least one of the plurality of optic fibers and obtaining optical scattering and absorption spectroscopy measurements;
   performing optical coherence domain reflectometry at the suspect tissue region using at least one of the plurality of optic fibers and obtaining optical coherence domain reflectometry measurements;
   comparing the optical scattering and absorption spectroscopy measurements taken adjacent to the skin surface to the optical scattering and absorption spectroscopy measurements taken at the suspect tissue region;
   comparing the optical coherence domain reflectometry measurements taken adjacent to the skin surface to the optical coherence domain reflectometry measurements taken at the suspect tissue region;
   indicating to a user a change in the optical scattering and absorption spectroscopy measurements based on the comparison of optical scattering and absorption spectroscopy measurements or a change in the optical coherence domain reflectometry measurements based on the comparison of optical coherence domain reflectometry measurements that is indicative of abnormal tissue.

* * * * *